United States Patent [19]

March et al.

[11] Patent Number: 5,797,870
[45] Date of Patent: Aug. 25, 1998

[54] PERICARDIAL DELIVERY OF THERAPEUTIC AND DIAGNOSTIC AGENTS

[75] Inventors: Keith L. March; Douglas P. Zipes, both of Carmel, Ind.

[73] Assignee: Indiana University Foundation, Bloomington, Ind.

[21] Appl. No.: 487,729

[22] Filed: Jun. 7, 1995

[51] Int. Cl.$^6$ .................................. A61M 31/00
[52] U.S. Cl. ....................... 604/49; 604/28; 604/53; 604/93; 128/898
[58] Field of Search ................ 604/28, 49, 53, 604/174, 176, 181, 93, 280, 264; 607/119–123; 128/642–644, 898

[56] References Cited

U.S. PATENT DOCUMENTS

| | | |
|---|---|---|
| 4,840,793 | 6/1989 | Todd, III et al. . |
| 4,884,567 | 12/1989 | Elliott et al. . |
| 4,935,234 | 6/1990 | Todd, III et al. . |
| 4,991,578 | 2/1991 | Cohen . |
| 5,269,326 | 12/1993 | Verrier . |
| 5,328,470 | 7/1994 | Nabel et al. . |
| 5,405,376 | 4/1995 | Mulier et al. . |
| 5,552,309 | 9/1996 | March . |

FOREIGN PATENT DOCUMENTS

| | | |
|---|---|---|
| 2 183 661 | 6/1987 | United Kingdom . |
| WO 89/06694 | 7/1989 | WIPO . |
| 9600112 | 1/1996 | WIPO . |

OTHER PUBLICATIONS

Wilensky, et al., Trends Cardiovasc. Med., vol. 3, No. 5, pp. 163–170 (1993).
Barr, et al., Trends Cardiovasc. Med., vol. 4, No. 2, pp. 57–63 (1994).
Barr, et al., Gene Therapy, vol. 1, pp. 51–58 (1994).
Joyce (1989) Gene 82:83.
Joyce and Inoue (1989) Nucleic Acids Research 17:711.
Ellington and Szostak (1990) Abstract of papers presented at the 1990 meeting and RNA Processing, Cold Spring Harbor Laboratory, Cold Spring Harbor, NY, p. 226.
Hendrickson et al. (1995) NAR 23:522.
Hibma et al. (1994) NAR 22:3806.
Kinzler and Vogelstein (1989) Nucleic Acids Research 17:3645.
Kramer et al. (1974) J. mol. Biol. 89:719.
Levisohn et al. (1969) PNAS 63:805.
Levisohn et al. (1969) PNAS 60:866.

(List continued on next page.)

Primary Examiner—Mark Bockelman
Assistant Examiner—Jennifer R. Sadula
Attorney, Agent, or Firm—Elliot M. Olstein; Raymond J. Lillie

[57] ABSTRACT

A method for treating a patient's heart which comprising delivering a gene therapy agent into the pericardial sac around the patient's heart. The agent is introduced surgically or by transvascular means such as a catheter which has been introduced percutaneously or otherwise. Introducing the gene therapy agent into the pericardial sac contains the agent, allowing high concentration of the agent adjacent large regions of the epicardium and pericardium without spillage or systemic distribution to other organs or tissues. The gene therapy agents of this invention comprise vectors for transferring genetic information to the epicardial cells in vivo or harvested cells which have been genetically engineered in vitro. In a preferred embodiment, a catheter is percutaneously introduced, such as through the femoral artery, and guided upstream into the left ventricle. The distal end of the catheter advanced until it penetrates through the epicardium so that agent can be introduced into the pericardial space. Access to the pericardium may also be gained intraoperatively or through a thoracotomy. Additionally, the method may comprise employing a viscosity enhancer in conjunction with the gene therapy agent to affect the kinetics of the agent-host cell interaction and thus improve the rate and efficiency of transduction.

25 Claims, 1 Drawing Sheet

OTHER PUBLICATIONS

Oliphant et al. (1989) Mol. Cell. Biol. 9:2944.
Oliphant and Struhl (1988) Nucleic Acids Research 16:7673.
Oliphant and Struhl (1987) Methods in Enzymology 155:568.
Oliphant et al. (1986) Gene 44:177.
Robertson and Joyce (1990) Nature 344:467.
Thiesen and Bach (1990) Nucleic Acids Research 18:3203.

PERICARDIAL DELIVERY OF THERAPEUTIC AND DIAGNOSTIC AGENTS

BACKGROUND OF THE INVENTION

This invention is directed to a method and system for treating a patient's heart with therapeutic or diagnostic agents. More particularly, it involves delivery of agents within the pericardial sac surrounding the patient's heart for genetic modification of the pericardial and epicardial cells.

Targeted delivery of a gene therapy agent without systemic dispersement thereof is a desirable but often difficult goal. Potential benefits include more efficient use of such agents and limitation of genetic modification to the desired area. However, the problems that must be overcome are significant: access to the delivery site, transporting the agent to the desired desired site; minimization of systemic loss, keeping the agent within a desired area; and timing, ensuring a sufficient quantity of the agent is available in the desired area for sufficient period of time to achieve the desired therapeutic or diagnostic effects.

In somatic gene therapy, cells in a desired region of the body are engineered to express a gene corresponding to a therapeutically or diagnostically useful protein. Genetic information necessary to encode and express the protein is transferred to the cells by any of a number of techniques, including viral vectors, electroporation, receptor-mediated uptake, liposome masking, precipitation, incubation and others. Gene therapy can be a direct in vivo process where genetic material is transferred to cells in the desired region of the patient's body. A current in vivo strategy relies on viral vectors. Alternatively, the process can be an indirect in vitro process where cells from the desired region are harvested, genetic material is transferred to the cells, and the cells are implanted back into the patient's body. In vitro techniques allow for more flexibility in transfer methods and may be safer since viral vectors need not be introduced into the patient's body, thus avoiding the theoretical risk of insertional mutations, replication reactivation and other harmful consequences. However, not all tissues are susceptible to harvesting and implantation and require an in vivo technique. The engineered cells can secrete the protein for a significant period of time, ensuring its supply in the target region. For example, human adenosine deaminase was expressed in vivo by rat vascular smooth muscle cells for over six months. Lynch CM et al., Proc. Natl. Acad. Sci. USA 89:1138-42 (1992).

One region of interest for gene therapy is the circulatory system. Researchers have transferred genetic material to the vascular walls, particularly the smooth muscle and endothelial cells. Suitable delivery techniques include temporary interruption of blood flow of the target vessel by ligation (Lynch et al., supra.), isolation of the target vessel with dual-balloon catheters (Leclerc G et al., J. Clin. Invest. 90:936-44 (1992)), use of perforated balloon catheters (Flugelman MY et al., Circulation 85:1110-17 (1992)), stents seeded with transduced endothelial cells (Dichek D. A. et al., Circulation 80:1347-53 (1989)) or vascular grafts lined with transduced endothelial cells (Wilson J. M. et al., Science 244:1344-46 (1989).

However, these methods have not been found suitable for treatment of the heart muscle. Thus far, experimental gene therapy in rats has been achieved through direct injection of DNA into the myocardium. Lin H. et al., Circulation 82:2217-21 (1992) and Acsadi G. et al., New Biologist 3:71-81 (1991). In these studies, direct injection caused inflammation, apparent myocyte necrosis and scar tissue along the needle tracks. When compared to injection of plasmid DNA, gene transfer by injection of adenovirus vectors was markedly more efficient. Guzman RG et al., Circulation Research 73:1202-7 (1993). Gene transfer using adenovirus vectors injected into pig hearts was highly efficient in regions immediately adjacent the injection, but evidence of gene transfer was found only in small region of the myocardium. French BA et al., Circulation 90:2414-24 (1994). As in the studies above, a prominent inflammatory response was associated with the injection. There remains a need for effective gene therapy methods for the heart.

Another difficulty associated with gene therapy is the need to transfer an effective amount of the genetic material in a clincally relevant time period. Exemplary techniques for introduction of engineered endothelial or smooth muscle cells or for in vivo gene transfer require total occlusion of the vessel for 30 minutes. Nabel E. G. et al., Science 249:1285-88 (1990); Nabel E. G. et al., Science 244:1342-44 (1989); and Plautz G. et al., Circulation 83:578-83 (1991). These time frames would not be feasible for delivery involving the heart due to myocardial injury during prolonged vascular occlusion. A study attempting to shorten these times employed a perforated balloon catheter and successfully delivered retroviral vectors within one minute, but achieved fewer than 100 transduced cells in a two cm segment of tissue. Flugelman et al., supra. Accordingly, there remains a need to provide gene therapy methods for treating the heart and coronary vasculature that effect sufficient genetic modification of large areas of the heart.

SUMMARY OF THE INVENTION

This invention is directed to a method for treating a patient's heart which comprises delivering a gene therapy agent into the pericardial sac around the patient's heart. The delivery may be made surgically or by transvascular means such as a catheter which has been introduced percutaneously or otherwise. Introducing the gene therapy agent into the pericardial sac contains the agent, allowing high concentration of the agent adjacent large regions of the epicardium and pericardium without spillage or systemic distribution to other organs or tissues. The gene therapy agents of this invention comprise vectors for transferring genetic information to the epicardial cells in vivo or harvested cells which have been genetically engineered in vitro. The sac also keeps the agent in contact with the desired region of the pericardium or epicardium for a useful period of time. When employing an in vivo technique, this is long enough to achieve efficient transduction or transfomation of the heart cells. With an in vitro technique, a useful time period allows the injected cells to implant and integrate into the heart tissue.

In a preferred embodiment, a catheter is percutaneously introduced, such as through the femoral artery, and guided upstream into the left ventricle. The distal end of the catheter comprises a hypotube configured as a helical coil. The catheter also comprises a torque transmitting shaft so that the hypotube may be screwed into the heart wall. The hypotube is advanced until it penetrates through the epicardium so that agent can be introduced into the pericardial space. A suitable device is shown in U.S. Pat. No. 5,405,376, which is hereby incorporated in its entirety by reference.

In other embodiments, the method involves percutaneously guiding a catheter downstream through one of the venae cavae to the right atrium. Once inside the right atrium, the catheter is passed into the right auricle. The wall at the apex of the right auricle is then pierced with the catheter, and the catheter is advanced into the pericardial space. Alternatively, a catheter may be introduced to the right atrium and penetrate the lateral atrial wall to gain access to the pericardial space. Access to the pericardium may also be gained intraoperatively, by sub-xiphoid entry or through a thoracotomy. Preferably, the thoracotomy should be minimal, through an intercostal space. Thoracoscopic, fluoroscopic or ultrasonic visualization may be employed to facilitate the procedure.

In each instance, the gene therapy agent is introduced by the catheter into the pericardial space to provide high concentration of the agent adjacent the epicardium for a useful period of time. Additionally, the method may comprise employing a viscosity enhancer in conjunction with the gene therapy agent to affect the kinetics of the agent-host cell interaction and thus improve the rate and efficiency of transduction.

Simple catheters in addition to the one described above may be used for percutaneous access, generally in conjunction with a guiding catheter. The tip of the catheter may be configured to pierce the heart wall, preferably the left ventricle to access the pericardial space. Alternatively, a device disposed within the lumen of the catheter may be so configured. For transthoracic access, it may be helpful to provide a more complex catheter or device. For example, a catheter may be used that attaches to the pericardium to pull it away from the epicardium, allowing the pericardium to be pierced without damaging the pericardium. Alternatively, the catheter may be configured to inject a fluid into the pericardial space to distend the pericardium away from the epicardial wall prior to penetrating the wall. The pericardial sac may be closed with sutures or other suitable means for sealing the pericardium.

DETAILED DESCRIPTION OF THE INVENTION

Figure 1:
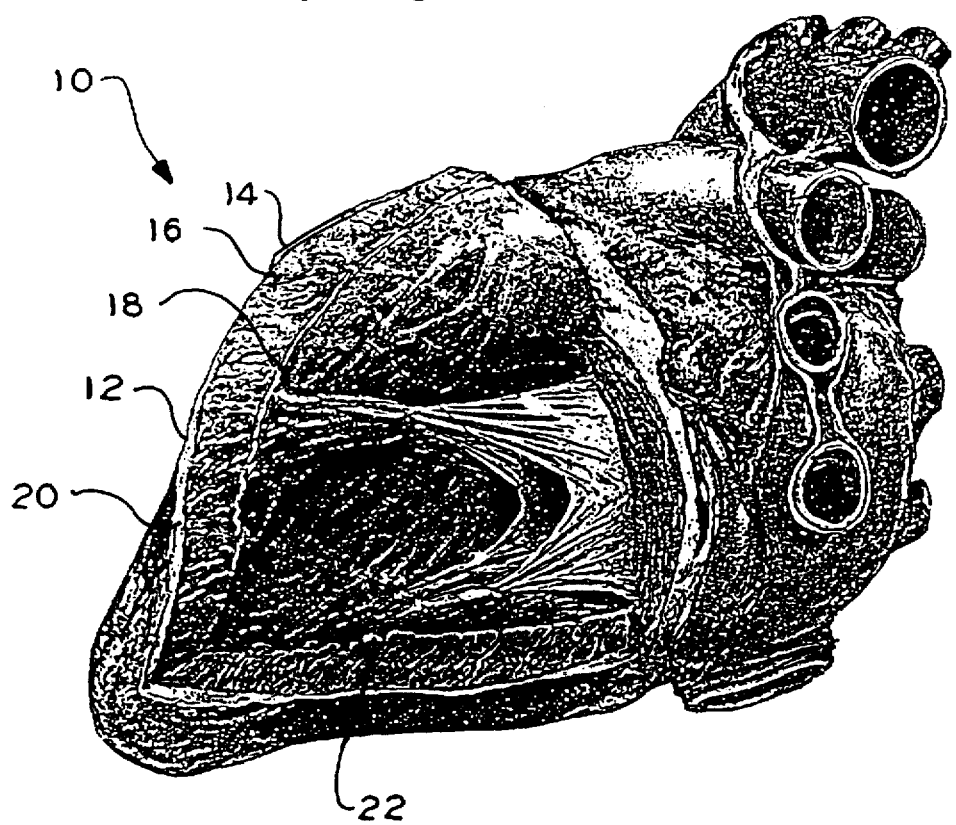
FIG. 1 is a schematic representation of a patient's heart.

The invention is a method for effecting gene therapy selectively, efficiently and over a wide area of the heart via the pericardial space. The method takes advantage of the fact that the pericardial sac isolates the heart such that it may be treated with a gene therapy agent separately from the remainder of the body while retaining the gene therapy agent locally for useful periods of time. FIG. 1 shows a heart 10 isolated from the body. The pericardium 12 or pericardial sac encases the cardiac muscle which comprises the epicardium 14, myocardium 16 and endocardium 18 and defines the pericardial space 20. Percutaneous access to the pericardial space 20 can be gained by a catheter advanced to a chamber of the heart, preferably the left ventricle 22, but the right atrium or other chamber may be suitable. The catheter then sequentially penetrates the endocardium 14, the myocardium 16 and the epicardium 18 to reach the pericardial space 20. Intraoperative access is achieved by a thoracotomy or by opening the chest wall. A suitable device is used to penetrate the pericardium 12 to reach the pericardial space 20.

Figure 2:
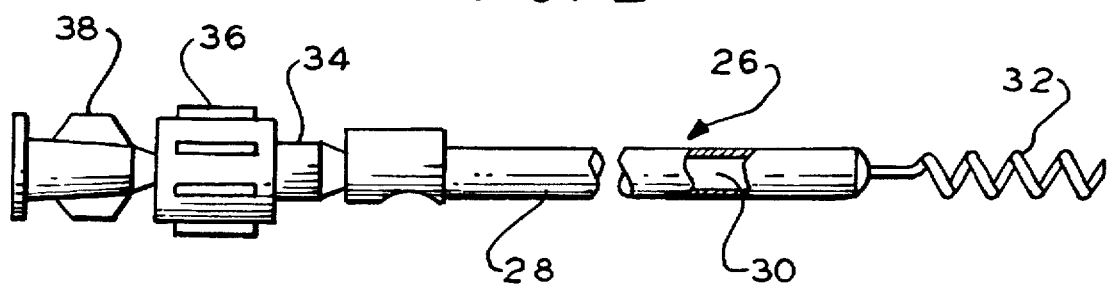
FIG. 2 is an elevational view, partially in section, of an intravascular device useful in the practice of the invention.

FIG. 2 illustrates a preferred intravascular device 26 useful for delivering gene therapy agent to the pericardial space 20. The device 26 comprises an elongated shaft 28 defining a lumen 30. Shaft 28 is constructed in conventional manner to be torque transmitting. At the distal end of shaft 28 is a helical hypotube 32 in fluid communication with lumen 30. The distal end of hypotube 32 is configured to pierce the heart muscle. A luer lock 34 at the proximal end of shaft 28 connects to a swivel mount 36 and is in fluid communication with lumen 30. A luer lock 38 also in fluid communication with lumen 30 connects to swivel mount 36 to allow introduction of gene therapy agent into lumen 30 by conventional means.

Device 26 is percutaneously introduced by means of conventional cut down techniques in the patient's arterial system, generally through the femoral artery. A guiding or shielding catheter (not shown) may be employed to facilitate introduction of the distal end of device 26 into the patient's left ventricle. Hypotube 32 is positioned against a desired area of the heart muscle in left ventricle 22. Torque is applied to swivel mount 36 and transmitted through shaft 28 to screw helical hypotube 32 through endocardium 14, myocardium 16 and then epicardium 18 to access pericardial space 20. A suitable, conventional device connected to luer lock 38 introduces gene therapy agent into lumen 30 for delivery through hypotube 32 into the pericardial space 20. The helical configuration of hypotube 32 helps anchor it in the heart muscle during delivery of the agent. The longer length of the helical tube compared to a straight tube also helps prevent backflow. Additionally, the helical penetration of the heart muscle tends to be self-sealing when the hypotube is removed.

In an different embodiment, the method of the invention comprises access to the pericardial space through the right atrium. The right atrium lies tangential to and between the pericardium and the epicardium. A conventional catheter (not shown) guided into the right atrium will be positioned substantially in parallel with the wall of the pericardium. This allows piercing the wall of right atrium by the catheter substantially without risk of damage to either the pericardium or the epicardium. Further, the right atrium is a thin-walled, low pressure, ear-like lobe which can be readily penetrated. Because it is a low-pressure area of the venous system, the risk of hemorrhage is low. In addition, the funnel-like shape of the right atrium facilitates catheter placement with minimal effort. The wall of the right atrium may be pierced with the catheter itself, or with an instrument passed through the lumen of the catheter. The catheter may be passed into the pericardial space through the opening in the wall of the atrium, or an instrument passed through the lumen of the catheter may be passed into the pericardial space.

Alternatively, access to the pericardium is gained intraoperatively, by sub-xiphoid entry or through a thoracotomy, or by open heart surgery. Preferably, the thoracotomy should be minimal, through an intercostal space for example. In such embodiments, a more complex, but conventional, device may be employed. It is preferable to provide a device that first pulls the pericardial sac away from the epicardium to facilitate penetration of the pericardium without damage to the epicardium. Thoracoscopic, fluoroscopic or ultrasonic visualization may be employed to facilitate the procedure. Gene therapy agent is introduced into the pericardial space, the device is removed and the penetration of the pericardium may be sutured or closed in other suitable manner to seal in the agent.

It is believed that abrasion of the epicardial or pericardial tissue may aid in absorption of the agent. Accordingly, it may be desirable to cause such abrasion or employ a catheter that allows selective abrasion.

Once access to the pericardial space has been gained, gene therapy agents may be introduced to treat the heart muscle without systemic dillution or unwanted effect on other organs of the body. Agents comprise naked DNA or DNA compositions for delivery of genetic information in vivo or cells which have been genetically modified in vitro. Methods for transfer of genetic information generally fall into one of three categories. First, DNA may be delivered by physical means, including microinjection, electroporation, biobalistic or particle bombardment, jet injection, and others. Second, DNA may be delivered by chemical means, using calcium phosphate, DEAE dextran, polylysine conjugates, "starburst" dendrimer conjugates, polybrene-dimethyl sulfoxide, receptor-mediated uptake systems such as asialoglycoprotein and transferrin, liposomes, virion like particles (VLP's), intra-cellular targeting ligands and others. Third, DNA may be delivered by biological means, including retroviral vectors such as Moloney murine leukemia virus (MoMLV), adenovirus vectors and adeno-associated virus vectors (AAV), herpes simplex virus vectors, semliki forest virus vectors, sindbis virus vectors and others.

Adenoviral vectors would include first-generation deletion mutant vectors as well as second, third and higher generation vectors. The other vectors similarly may be sub-categorized and each are considered useful agents for the practice of the invention. Combinations of the above methods may also be useful.

A preferred embodiment of the invention comprises delivering a replication-deficient, first generation adenvovirus vector (Av1) expressing fibroblast growth factor 5 into the pericardial space. Generally, a vector should be delivered at a concentration of between about $10^6$ and about $10^{10}$ infectious units/ml and preferably between about $10^8$ and about $10^9$ infectious units/ml of carrier fluid. A total amount of injected fluid may range from about 1 to about 15 ml. The agent should achieve effective transfer in from about 1 to 10 minutes and preferably in about 1 to 2 minutes.

In a some embodiments, the gene therapy agent is mixed with a pharmaceutically acceptable carrier such as a viscous biocompatible polyol to maintain prolonged, high pericellular agent concentration. For example, poloxamer 407 combined with an Av1 vector achieves high rates of transduction in bovine aortic smooth muscle cells. March K. L. et al., "Pharmacokinetics of Adenoviral Vector-Mediated Gene Delivery to Vascular Smooth Muscle Cells: Modulation by Poloxamer 407 and Implications for Cardiovascular Gene Therapy," *Human Gene Therapy* 6:41–53 (1995). Other viscosity modifying compounds are suitable as well. For example, the agent could comprise a first compound which, by itself, does not significantly change the viscosity. However, mixing with a second compound causes a polymerization or other viscosity-enhancing reaction. The second compound could be mixed with the agent prior to delivery, injected simulataneously or added after injection of the agent.

An agent suitable for these methods and others may be delivered into the pericardial space for in vivo gene transfer. Alternatively, each of these methods and others may be employed to produce an agent comprising harvested cells genetically modified in vitro. The modified cells may then be introduced into the pericardial space to integrate into the epicardium and pericardium. Selection of an in vitro or in vivo technique depends in part upon the type of treatment desired. Retroviral vectors typically require dividing cells for efficient transfer and are not available in titers as high as adenoviral vectors. However, retroviral vectors insert the genetic information into the host DNA which can result in stable integration into the genome. Adenovirus vectors express the transferred gene in a non-integrating fashion. Accordingly, selection between the two vectors may depend in part on whether the desired activity is to be acute or chronic and the nature of the target tissue.

Successful in vivo transfer or integration of modified cells turns the pericardial sac into a secreting organ capable of expressing the desired genetic information and providing enhanced coating and penetration of the cardiac tissue. Examples of useful therapeutic genes are angiogenic factors such as vascular endothelial growth factor (VEGF), acidic and basic fibroblast growth factors (aFGF, bFGF) and angiogenin. These factors are useful for enhancing collateral formation of vasculature by inducing angiogenesis to relatively ischemic areas of myocardial tissue. Other useful genes are those responsible for controlling nitric oxide production such as nitric oxide synthase. Such genes could be used to reduce the restenotic response or enhance the vasodilation resonse. Control of vasodilation may permit treatment of angina. The effects of nitric oxide on neural conduction and action potentials may be exploited to modulate arrhythmogenesis. Genes expressing prostaglandin synthetic enzymes such as prostaglandin synthase may be used to effect local generation of prostaglandins to influence neural conduction and cardiac arrhythmogenesis, as well as causing vasodilation and reducing vascular proliferation following injury. Yet other useful genes include those expressing isoforms of superoxide dismutase and other antioxidant proteins. These genes could confer protection in the case of myocardial ischemia. Similarly, incorporation of appropriate genetic information may allow alterations in inotropy and anti-inflammatory or anti-infective treatment of intra-pericardial disease processes, including autoimmune disease, cancer and infection. One of skill in the art will recognize that many other genes may be useful in the practice of this invention.

Effective transfer of genetic material employing the methods of this invention has been demonstrated in canine modeling. Av1 vectors were used to deliver luciferase, nuclear-targeted β-galactosidase (β-gal) or human α1-antitrypsin (h-aT). The vectors were delivered to the pericardial space using either transvenous or transthoracic access under direct visualization. Luciferase expression was apparent in the pericardial sac and the epicardium with little expression in the myocardium and almost no signal was detected in the liver. β-gal staining indicated nearly 100% expression in the pericardial sac, an unprecedented level of efficiency for tranduction, and patchy, superficial expression was observed in the epicardium. Finally, h-aT was found in high concentration in the pericardial fluid, but not in the serum or control fluids. These results demonstrate the feasibility of efficient gene transfer by employing the pericardial sac to contain the gene therapy agent for a useful period of time.

The invention has been described herein primarily with reference to the preferred embodiments. However, it should be recognized that the invention applies to genetic modification and treatment of the heart in general and that various modifications and improvements can be made to the invention without departing from the scope thereof.

What is claimed is:

1. A method for delivering a gene therapy agent to epicardial and pericardial tissue of a patient's heart, comprising:

providing an elongated intravascular device having a distal tip configured to pierce a wall of the patient's heart.

guiding the distal tip of the device into the left ventricle of the patient's heart;

piercing the endocardium, the myocardium and the epicardium with the distal tip of the device, said distal tip being located in the pericardial space;

introducing the gene therapy agent through the distal tip; and maintaining the gene therapy agent within the pericardial space for a sufficient period of time.

2. The method of claim 1, wherein the step of maintaining the gene therapy agent within the pericardial space comprises providing the intravascular device with a helical hypotube distal tip.

3. A method of delivering a gene therapy agent to epicardial and pericardial tissue of a patient's heart, comprising:

providing a device configured to be introduced through the patient's chest having a distal tip configured to pierce the pericardium of the patient's heart;

pulling the pericardium away from the epicardium;

piercing the pericardium with the distal tip of the device;

positioning the distal tip of the device in the pericardial space;

introducing the gene therapy agent through the distal tip into the pericardial space; and maintaining the gene therapy agent within the pericardial space for a sufficient period of time.

4. The method of claim 3, wherein the step of maintaining the gene therapy agent within the pericardial space comprises suturing the pericardium after removing the distal tip.

5. The method of claim 4, wherein the step of maintaining the gene therapy agent within the pericardial space comprises mixing the gene therapy agent with a viscosity modifying component.

6. The method of claim 5, wherein the step of maintaining the gene therapy agent within the pericardial space comprises mixing the gene therapy agent with a viscous biocompatible polyol.

7. A method for genetically modifying cells lining the pericardial space of a patient's heart, comprising delivering a gene therapy agent into the pericardial space defined by the epicardium and the pericardium surrounding the patient's heart thereby transferring DNA to cells lining the pericardial space with the agent.

8. The method of claim 7, wherein the step of delivering the gene therapy agent comprises delivering an agent comprising a vector containing DNA capable of expressing a therapeutically or diagnostically useful protein.

9. The method of claim 8, wherein the step of delivering the gene therapy agent comprises delivering a vector selected from the group consisting of retroviral vectors, adenovirus vectors, adeno-associated virus vectors, herpes simplex virus vectors, semliki forest virus vectors, and sindbis virus vectors.

10. The method of claim 9, wherein the step of delivering the gene therapy agent comprises delivering a vector containing DNA capable of expressing proteins selected from the group consisting of vascular endothelial growth factor, acidic and basic fibroblast growth factors, angiogenin, other angiogenic and vasculogenic factors, nitric oxide synthase, prostaglandin synthase and other prostaglandin synthetic enzymes and superoxide dismutase and other antioxidant proteins.

11. The method of claim 8, wherein the step of delivering the gene therapy agent comprises:

a) providing an elongated intravascular device having a distal tip configured to pierce a wall of the patient's heart;

b) guiding the distal tip of the device into a chamber of the patient's heart;

c) piercing the endocardium, the myocardium and the epicardium with the distal tip of the device the distal tip is located in the pericardial space; and d) introducing the gene therapy agent through the distal tip.

12. A gene therapy method for cells lining the pericardial space of a patient's heart comprising:

a) harvesting epicardial or pericardial cells from the heart of a patient;

b) genetically modifying the cells;

c) selecting cells which have been successfully modified;

d) delivering the selected cells into the pericardial space.

13. The method of claim 12 wherein step (b) comprises genetically modifying said cells by introducing into said cells an agent comprising a vector including DNA encoding a therapeutically or diagnostically useful protein.

14. The method of claim 13 wherein said vector is selected from the group consisting of retroviral vectors, adenovirus vectors, Herpes Simplex Virus vectors, Semliki Forest Virus vectors, and Sindbis virus vectors.

15. The method of claim 13 wherein said therapeutically useful protein is selected from the group consisting of vascular endothelial growth factor, acidic fibroblast growth factors, basic fibroblast growth factors, angiogenic factors, vasculogenic factors, nitric oxide synthase, prostaglandin synthetic enzymes, and antioxidant proteins.

16. A method for treating a patient's heart, comprising:

combining a gene therapy agent with a first compound, said first compound being a pharmaceutically acceptable carrier, to form thereby a mixture of said gene therapy agent and said first compound;

injecting said mixture of said gene therapy agent and said first compound into the pericardial space of the patient's heart; and injecting into the pericardial space a second compound to enhance the viscosity of said mixture of said gene therapy agent and said first compound.

17. The method of claim 16 wherein said gene therapy agent comprises a vector including DNA encoding a therapeutically useful protein.

18. The method of claim 17 wherein said vector is selected from the group consisting of retroviral vectors, adenovirus vectors, Herpes Simplex Virus vectors, Semliki Forest Virus vectors, and Sindbis virus vectors.

19. The method of claim 17 wherein said therapeutically useful protein is selected from the group consisting of vascular endothelial growth factor, acidic fibroblast growth factors, basic fibroblast growth factors, angiogenic factors, vasculogenic factors, nitric oxide synthase, prostaglandin synthetic enzymes, and anti-oxidant proteins.

20. The method of claim 16 wherein said second compound is injected simultaneously with said mixture.

21. The method of claim 16 wherein said second compound is injected after the injection of said mixture.

22. A method of treating a patient's heart, comprising:

combining a gene therapy agent with (i) a first compound, said first compound being a pharmaceutically acceptable carrier, and (ii) a second compound, said second compound being a viscosity enhancing agent, to form thereby a mixture of said gene therapy agent, said first compound, and said second compound; and injecting said mixture of said gene therapy agent, said first compound, and said second compound into the pericardial space of the patient's heart.

23. The method of claim 22 wherein said gene therapy agent comprises a vector including DNA encoding a therapeutically useful protein.

24. The method of claim 23 wherein said vector is selected from the group consisting of retroviral vectors, adenovirus vectors, Herpes Simplex Virus vectors, Semliki Forest Virus vectors, and Sindbis virus vectors.

25. The method of claim 23 wherein said therapeutically useful protein is selected from the group consisting of vascular endothelial growth factor, acidic fibroblast growth factors, basic fibroblast growth factors, angiogenic factors, vasculogenic factors, nitric oxide synthase, prostaglandin synthetic enzymes, and anti-oxidant proteins.

* * * * *